United States Patent [19]

Eisenstadt et al.

[11] Patent Number: 5,187,303
[45] Date of Patent: Feb. 16, 1993

[54] PROCESS FOR THE PREPARATION OF OCTYL METHOXY CINNAMATE

[75] Inventors: Amihai Eisenstadt, Ramat-Hasharon; Yehuda Keren, Kiryat Motzkin, both of Israel

[73] Assignee: IMI (TAMI) Institute for Research and Development Ltd., Haifa, Israel

[21] Appl. No.: 868,042

[22] Filed: Apr. 14, 1992

[30] Foreign Application Priority Data

Apr. 15, 1991 [IL] Israel .......................... 97850
Mar. 31, 1992 [IL] Israel ........................ 101430

[51] Int. Cl.$^5$ .............................................. C07C 69/76
[52] U.S. Cl. ............................................... 560/55
[58] Field of Search ........................................ 560/55

[56] References Cited

FOREIGN PATENT DOCUMENTS 871746 5/1971 Canada .
0044975 2/1982 European Pat. Off. .
1278406 6/1972 United Kingdom .

OTHER PUBLICATIONS

Tour, J. M. et al., J. Org. Chem. 55(11) 3452-3, 1990.
Abedi, J. et al., Synth. Comm. 19(9-10) 1539-49, 1989.

*Primary Examiner*—Paul J. Killos
*Attorney, Agent, or Firm*—Merchant & Gould, Smith, Edell, Welter & Schmidt

[57] ABSTRACT

Octyl methoxy cinnamate of the formula

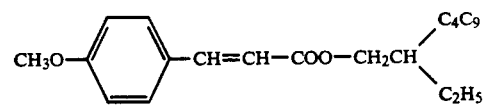

is prepared by reacting p-bromoanisole with octyl-acrylate in an inert solvent, in the presence of a base and of a coupling catalyst.

14 Claims, No Drawings

PROCESS FOR THE PREPARATION OF OCTYL METHOXY CINNAMATE

FIELD OF THE INVENTION

The present invention relates to a process for the preparation of octyl methoxy cinnamate. More particularly the invention relates to an economic and efficient process in which octyl methoxy cinnamate is prepared by a catalytic coupling reaction.

BACKGROUND OF THE INVENTION

Octyl p-methoxy cinnamate, is referred to hereinafter as OMC for the sake of brevity, and has the formula:

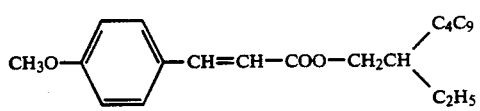

OMC is a well known sunscreening agent and along with other sunscreening products, is used to protect the skin from skin diseases due to the sun, particularly skin cancer. OMC is one of the most widely used ultra violet (UV) sunscreeners, and its importance in this field is increasing steadily.

The Prior Art

Various processes are known in the art, which involve cinnamic acid derivatives. For instance, European Patent No. 856.411, is directed to the preparation of methoxy alkyl esters of p-methoxycinnamic acid, by the reaction of alkyl p-methoxy cinnamate with an alcohol in the presence of alkoxide (transesterification process). In other processes, rather than starting from the methoxy cinnamate, cinnamic acid esters are prepared by reacting styrene with aliphatic alcohols, CO and oxygen in the presence of catalysts (Japan Kokai JP 60,126,245).

The major route for preparing OMC passes through the preparation of p-methoxy cinnamic acid (p-MCA) [Zh. Org. Khim. 25 (9), 1876 (1989)], and starts from anisaldehyde which is both expensive and rather difficult to synthesize. Furthermore, the use of p-MCA, or the corresponding low-alcohol esters, as a raw material, requires an extra step to form OMC, viz., esterification or transesterification. The preparation of OMC is described in EP 229,394 and in U.S. Pat. No. 4,713,473 which teaches to heat OMC in the presence of a phenol to insure that the ester is considered Ames negative.

It is an object of the present invention to provide a simple and economic process, which can be used to produce OMC in good yields and purity.

It is another object of the invention to provide a process which employs easily available and inexpensive starting materials.

It has further been found, and this is an object of the present invention, that it is possible to prepare OMC of good quality and which tests Ames negative, while carrying out a preparation process substantially in the absence of any added antioxidant. Furthermore it has been found, and this is another object of the invention, that it is not necessary to add antioxidants, such as BHT, to the reaction mixture resulting from the process of the invention when distilling OMC therefrom, and that OMC distilled from the reaction mixture so obtained, without adding any substantial amount of antioxidant, tests Ames-negative.

The term "added antioxidant" is meant to indicate substantial amounts of antioxidant added in the course or for the purpose of the reaction, or during work-up of the final product, but should not be taken to include small amounts of antioxidants which can normally be present in the commercial reactants. As will be apparent to the skilled person, some antioxidants are often present in various raw materials, for the purpose of improving their shelf life, to inhibit polymerization, etc. Such small amounts are not considered "added antioxidant", as meant herein.

The process for the preparation of octyl methoxy cinnamate according to the invention comprises reacting p-bromoanisole with octyl-acrylate in an inert solvent, in the presence of a base and of a coupling catalyst. Preferably, the solvent is an aprotic polar solvent, more preferably N-methyl-pyrrolidone. This process can be schematically written as follows:

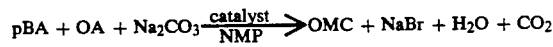

While, as stated, no added antioxidant is required for carrying out the invention, the addition of an antioxidant to the reaction mixture, if effected for any reason, e.g., to avoid or at least substantially to hinder, the polymerization of octyl-acrylate, during the coupling reaction, does not substantially affect the invention. Many known inhibitors can be used, but preferred antioxidants are, e.g., methyl hydroquinone and BHT. The reaction is preferably carried out in an inert atmosphere, to avoid reaction of octyl-acrylate with oxygen, preferably the inert atmosphere being substantially $N_2$ atmosphere, as oxygen may initiate free-radical polymerisation of the $\alpha,\beta$-unsaturated entities, and lead to the formation of undesirable by-products.

A further advantage of the process of the invention is that it is possible to utilize the catalysts and the solvents in subsequent batches, after a simple regeneration of the recovered catalyst and make-up of catalyst and solvent, as required.

Thus, as will be apparent to the skilled person, inter alia, the following advantages result from the invention, as compared, e.g., with prior art processes, such as that described in U.S. Pat. No. 4,713,473:

The necessity to purchase and handle an extra raw material, such as BHT, is eliminated.

The necessity to monitor BHT levels during the reaction is eliminated. This is true even if some amounts of BHT are added, as optionally possible and as explained above.

The work-up of the reaction mixture is simplified by eliminating the need to remove BHT at the end of the reaction.

It simplifies the handling of waste material.

It eliminates the need to add BHT continuously during the distillation of the final product.

The catalyst employed in the process of the invention is a palladium catalyst, preferably palladium supported on carbon, as well as a variety of palladium salts and complexes, such as, e.g., $PdCl_2$, $Pd(OAc)_2$ and $PdCl_2(Ph_3P)_2$. A convenient catalyst is a 5% Pd/C of the type manufactured by Fluka or Aldrich. While the desirable amount of catalyst employed varies substantially from one manufacturer to the other, and, as will be appreciated by the skilled chemist, even between two different batches of the same manufacturer, the desirable Br:Pd ratio will be in the order of 300–4000. In any case, the skilled chemist will easily determine the necessary amount of catalyst employed, for a specific type of catalyst. Examples of suitable solvents are N-methylpyrrolidone, dimethylformamide, N,N-dimethylacetamide and dimethylsulfoxide.

The reaction is carried out in the presence of a base which reacts with HBr formed in the reaction to form an inert material. The base is preferably selected from alkali bicarbonates and carbonates, such as $NaHCO_3$, $Na_2CO_3$ (and potassium salts), and organic amines such as tributylamine, and is present in a substrate:base ratio of between 1:1 and 1:2. The reaction can be carried out in a temperature range comprised between 160°–210° C., and is preferably carried out at temperature comprised between 180°–200° C.

It is desirable, though not imperative, to carry out the reaction in an inert atmosphere, to avoid possible reaction of octyl-acrylate with oxygen, which may lead to the formation of undesirable by-products.

As will be apparent to a person skilled in the art, the actual nature of the product, from the point of view of purity and by-products content, is very much dependent on the preparation method employed. Therefore, OMC prepared according to different processes may differ in critical contents of trace impurities. The preparation route may be responsible for the fact that OMC so prepared tests Ames-negative. Accordingly, OMC prepared according to the process of the invention, also forms a part of the present invention.

DETAILED DESCRIPTION OF PREFERRED EMBODIMENTS

The above and other characteristics and advantages of the process of the invention will be better understood from the following illustrative and non-limitative description of preferred embodiments thereof.

Ames Test Procedure

A Salmonella/mammalian microsome mutagenicity test was conducted to determine whether a DMSO test article solution of OCTYL METHOXY CINNAMATE (OMC) would cause mutagenic changes in histidine-dependent mutant strains of *Salmonella typhimurium*. The method of Ames et al. [Mutation Research 31 (1975), pp. 347-364] was followed.

After the solution was found to be noninhibitory to growth of the tester strains, aliquots of the test solution, negative control and positive control solutions were added to duplicate plates containing histidine-deficient medium. Separate plates were inoculated with the Ames *Salmonella typhimurium* tester strains TA98, TA100, TA1535, TA1537 and TA1538. The rate of mutation to nonhistidine-dependent wild types was determined for each plate; the spontaneous reversion rate for each strain in the presence of the DMSO blank was compared to the corresponding rate of reversion in the presence of the test article solution and in the presence of known mutagens.

The study was conducted in accordance with the United States requirements of Good Laboratory Practice (GLP) Regulations, as described in the U.S. Federal Register at 21 CFR 58.

Under the conditions described above, all tested DMSO solutions of OCTYL METHOXY CINNAMATE (OMC) did not cause mutagenic changes in the *Salmonella typhimurium* tester strains employed.

EXAMPLE 1

Preparation of OMC p-Bromoanisole (PBA, 187 g., 1 mole), sodium carbonate (57.7 g, 0.54 mole), octyl-acrylate (OA, 228 ml, 1.1 mole) and butylated hydroxytoluene (BHT, 0.66 g, 0.003 mole) were placed in a 4-necked 1 liter glass reactor containing 430 N-methylpyrrolidone (NMP). To the mixture there were added 5.13 g (2.216 mmol) of a 5% Pd/C catalyst (Aldrich, Cat. No. 20-568-0). The charged reactor was flushed with nitrogen for 15 minutes at ambient temperature and then heated for 2 hours under an $N_2$ atmosphere at 180° C. under vigorous stirring.

Analysis of the resulting mixture by uncalibrated GC revealed that OMC was formed in 96% conversion. The reaction mixture was cooled to 90° C. and filtered through a frit. The NMP solvent was removed under reduced pressure (170° C./25 mm Hg) and then unreacted raw material (PBA and OA) were distilled off. The product was then distilled at 186° C./0.6 mbar to give 241.5 g (86% of theoretical yield based on PBA) in a purity greater than 98%, as determined by HPLC. The recovered Pd/C waste contained 86.5% of the original Pd metal. The product was identified by GC-MS, $^1H$-NMR, UV and IR spectra, as well as by comparison of boiling point and refractive index. Comparison was made with a commercially available material.

The product so obtained was tested in the above-described Ames test, and found to be Ames-negative.

EXAMPLE 2

Preparation Using Recovered Catalyst and Solvent

A series of experiments was carried out in which 4 batches of OMC were prepared recycling the Pd/C and NMP each time. The Pd/C from the previous batch was washed with 1:1 HCl/water and acetone, then dried and used on a fresh batch of PBA with the addition of 10–20% fresh Pd/C and make-up of NMP with recovered solvent. The Br/Pd ratio was about 300, and the reaction temperature was maintained at 180° C. using an oil bath. The reaction mixture was stirred with a magnetic stirrer. The initial reaction conditions are detailed in Table I, and the results of each run are presented as uncalibrated GC results in Table II below. Only major components are listed.

TABLE I

| Component | gr. | mmols load |
|---|---|---|
| PBA | 7.47 | 40 |
| OA | 8.05 | 44 |
| BHT | 0.042 | 0.19 |
| Na2CO3 | 2.3 | 21.6 |
| NMP | 23 ml | |
| 5% Pd/C | 0.308 | |

TABLE II

| Cycle No. | Reaction time (mins) | PBA % | OA % | OMC % |
|---|---|---|---|---|
| 1 | 65 | 9.02 | 15.39 | 70.81 |
|   | 135 | 5.44 | 9.01 | 80.09 |
|   | 245 | 6.15 | 7.01 | 81.72 |
| 2 | 5 | 30.99 | 59.79 | 7.61 |
|   | 75 | — | 2.2 | 89.23 |
| 3 | 30 | 6.71 | 16.7 | 72.09 |
|   | 75 | — | 1.64 | 91.01 |

TABLE II-continued

| Cycle No. | Reaction time (mins) | PBA % | OA % | OMC % |
|---|---|---|---|---|
| 4 | 53 | — | 1.32 | 94.67 |

EXAMPLE 3

Preparation using different solvents

Example 1 was repeated, using dimethyl formamide (DMF), dimethylsulfoxide (DMSO) and dimethylacetamide (DMAA) as the solvent, instead of NMP. After about 8 hours the content of OMC in the reaction mixture was 24.6% with DMF, 51.15% with DMAA and 22.25% with DMSO. These results illustrate that NMP is the preferred solvent for reactions carried out at atmospheric pressure. In order to obtain higher reaction rates, e.g., with DMAA or DMF, reactions must be carried out in closed vessels at over-atmospheric pressures and at higher temperatures. The above results were obtained when carrying out the reaction at 150° C. with DMF, 165° C. with DMAA and 190° C. with DMSO.

EXAMPLE 4

OMC Production Using A Homogeneous Catalyst

A mixture of 4-bromoanisole (PBA, 5 g, 26.7 mmol), octyl acrylate (OA, 5.5 g, 29.8 mmol), palladium(II) acetate (0.045 g, 0.2 mmol), triphenylphosphine (150 g, 0.055 mmol) and sodium bicarbonate (1.1 g, 10.4 mmol) in DMF (10 ml) was heated at 120°-125° C. under an inert atmosphere for 18 hours. At the end of the heating cycle the reaction mixture was cooled to room temperature and poured in water, extracted with ethyl acetate (2×25 ml) and filtered through a celite pad to remove undissolved material. Concentration of the organic filtrate gave a heavy liquid (7.62 g). GC analysis of the crude product suggested that the reaction went with partial conversion and contained 88% OMC, based on reacted PBA.

EXAMPLE 5

Preparation of OMC

Example 1 was repeated, without the introduction of BHT. p-Bromoanisole (PBA, 187 g., 1 mole), sodium carbonate (57.7 g, 0.54 mole), and octyl-acrylate (OA, 228 ml, 1.1 mole) were placed in a 4-necked 1 liter glass reactor containing 430 N-methylpyrrolidone (NMP). To the mixture there were added 5.13 g (2.216 mmol) of a 5% Pd/C catalyst (Aldrich, Cat. No. 20-568-0). The charged reactor was flushed with nitrogen for 15 minutes at ambient temperature and then heated for 2 hours under an $N_2$ atmosphere at 180° C. under vigorous stirring.

Analysis of the resulting mixture by uncalibrated GC revealed that OMC was formed in 96% conversion, based on pBA. The reaction mixture was cooled to 90° C. and filtered through a frit. The NMP solvent was removed under reduced pressure (180° C./25 mm Hg) and then unreacted raw material (PBA and OA) were distilled off. The product was then distilled at 186° C./0.6 mbar to give 241.5 g (86% of theoretical yield based on PBA) in a purity greater than 98%, as determined by HPLC. The recovered Pd/C waste contained 70-85% of the original Pd metal. No substantial differences were found between the results obtained with or without BHT. OMC obtained in this example tested Ames-negative in the above Ames Test.

EXAMPLE 6

A 5-necked 3-liter glass reactor, equipped with mechanical stirrer, thermocouple, inlet gas adapter, Dean-Stark device and sampling-septum was loaded with 374 g (2M) p-BA, 404 (2.2M) OA, 106 g (1M) $Na_2Co_3$, 2.09 g (0.001028M) of 5% Pd/C and 376 ml NMP as a solvent. 5 Cycles of this were performed with the addition of 10% fresh catalyst through each of the first three cycles. The reactor was flushed with $N_2$, then the contents were heated to the reaction temperature (180°-190° C.). The reaction mixture was stirred under $N_2$ for two to three hours, while samples for G.C. follow-up detection were taken at intervals.

After this period, the reactor was cooled to 70°-90° C., and the catalysts and the salts cake were recovered by filtration. The salts were removed by aqueous extraction of the cake. The volatile components of the reaction mixture (NMP, p-BA, OA) were removed by distillation under a vacuum of 25 mm Hg, where OMC was distilled carefully in fractional column.

Analysis of the crude organic products (summary of 5 cycles), by GC method:

| | % |
|---|---|
| p-BA conversion | 79.4 |
| OMC selectivity | 88.1 |
| yield | 70 |
| Balance of material through the 5 runs | 90.5 |

EXAMPLE 7

Large-Scale Preparation

A series of 5 consecutive reactions were carried out in a Pfaudler glass-lined reactor, nominal volume 100 liters, stirring rate 200 rpm. The catalyst and solvent were recycled from the previous reaction.

| Component | Kg/batch |
|---|---|
| pBA | 33 kg |
| OA | 35 |
| NMP | 24 |
| $Na_2CO_3$ | 10 |
| Catalyst Pd/C | 1.0 |
| Br/Pd ratio | 1:3,700 |

The reaction mixture was heated through the jacket, whereby a slightly exothermic reaction started. The external heating rate was lowered and controlled to maintain a reaction temperature of 190°-200° C. during 2.5-3.5 hours.

The coupling reaction was accompanied by water formation. The water vapors were collected thorugh a condenser, together with some reaction components, such as NMP, pBA and OA. Composition of the final reaction mixture varied, depending on the catalyst activity (cycle):

| Component | Content |
|---|---|
| OMC | 44%-50% |
| NMP | 30%-35% |
| pBA | 3.5%-10.0% |

| Component | Content |
| --- | --- |
| OA | 2.0%–6% |

The analysis of the results revealed the following efficiencies based on pBA:

| | |
| --- | --- |
| Conversion | 74%–92% |
| Selectivity | 90%–92% |
| Yield | 66%–84% |

The crude reaction mixture was filtered to separate NaBr and catalyst. The filter cake was washed with solvent recovered from previous reactions, and the wash liquor reused in the next reaction. The filtrate was distilled (25 mm Hg, up to 170° C.) to remove NMP and excess raw materials. A part of the recovered solvent (as mentioned above) was used for washing the filter cake, and the other directly recycled to the next reaction.

The raw distillation product (65–70% OMC) was submitted to vaporization at 2–3 mmHg, up to 250° C. from the reactor, to separate lights (residual NMP and raw materials not recovered in the previous distillation stages) and heavy residue.

The vaporization product, containing 90–95% OMC, was submitted to fractional distillation (2–10 mm Hg, up to 250° C.) to obtain a final product of over 98% pure OMC. A representative product sample (from 5 cycles) was tested in the Ames test and found to be Ames-negative.

We claim:

1. A process for the preparation of octyl methoxy cinnamate of the formula

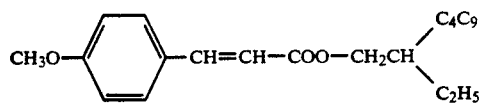

comprising reacting p-bromoanisole with octyl-acrylate in an inert solvent, in the presence of a base and of a coupling catalyst.

2. A process according to claim 1, wherein the solvent is an aprotic polar solvent.

3. A process according to claim 2, wherein the solvent is selected from N-methyl-pyrrolidone, dimethylformamide, N,N-dimethylacetamide and dimethylsulfoxide.

4. A process according to any one of claims 3, wherein the catalyst is a palladium catalyst.

5. A process according to claim 4, wherein the catalyst is 5% palladium, supported on carbon.

6. A process according to any one of claims 5, wherein the base is selected from $NaHCO_3$, $Na_2CO_3$, $KHCO_3$ and $K_2CO_3$.

7. A process according to any one of claims 6, wherein the reaction is carried out at a temperature comprised between 160°–210° C., preferably between 180°–200° C.

8. A process for the preparation of octyl methoxy cinnamate which tests Ames-negative, comprising reacting p-bromoanisole with octyl-acrylate in an inert solvent, in the presence of a base and of a coupling catalyst and substantially without adding any antioxidants during the reaction.

9. A process according to claim 1, further comprising the steps of:
 a) filtering the reaction mixture after the reaction has been substantially completed, to separate NaBr and the catalyst therefrom;
 b) distilling the filtrate to remove the solvent and excess raw materials;
 c) vaporizing the raw distillation product to separate light and heavy residues; and
 d) fractionally distilling the product so obtained to yield highly pure OMC product;
all the above steps being carried out without adding any substantial amount of antioxidant.

10. A process according to claim 7, in which an antioxidant is further added to hinder or avoid polymerization of octyl-acrylate.

11. A process according to claim 10, wherein the antioxidant is methyl hydroquinone or butylated hydroxyanisole.

12. A process according to claim 10, wherein the reaction is carried out in an inert atmosphere.

13. A process according to claim 12, wherein the inert atmosphere is an $N_2$ atmosphere.

14. A process according to any one of claims 13, comprising utilizing catalyst and solvent recycled from a previous batch.

* * * * *

UNITED STATES PATENT AND TRADEMARK OFFICE
CERTIFICATE OF CORRECTION

PATENT NO. : 5,187,303

DATED : February 16, 1993

INVENTOR(S) : Eisenstadt et al.

It is certified that error appears in the above-identified patent and that said Letters Patent is hereby corrected as shown below:

Title page, Abstract formula (57), "$C_4C_9$" should read --$C_4H_9$--

Column 1, line 17, "$C_4C_9$" should read --$C_4H_9$--

Column 7, line 39, "$C_4C_9$" should read --$C_4H_9$--

Column 8, line 5, delete "any one of claims" and insert therefor --claim--.

Column 8, line 9, delete "any one of claims" and insert therefor --claim--.

Column 8, line 12, delete "any one of claims" and insert therefor --claim--.

Column 8, line 45, delete "any one of claims" and insert therefor --claim--.

Signed and Sealed this

Eleventh Day of January, 1994

*Attest:*

BRUCE LEHMAN

*Attesting Officer*  *Commissioner of Patents and Trademarks*